United States Patent [19]

Munro

[11] Patent Number: 5,437,665
[45] Date of Patent: Aug. 1, 1995

[54] ELECTROSURGICAL LOOP ELECTRODE INSTRUMENT FOR LAPAROSCOPIC SURGERY

[76] Inventor: Malcolm G. Munro, 4135 Woodman Ave., Sherman Oaks, Calif. 91423

[21] Appl. No.: 134,106

[22] Filed: Oct. 12, 1993

[51] Int. Cl.[6] ............................................. A61B 17/39
[52] U.S. Cl. ........................................ 606/47; 606/45; 606/41
[58] Field of Search ................................. 606/37–41, 606/45–50; 128/642

[56] References Cited

U.S. PATENT DOCUMENTS

| | | | |
|---|---|---|---|
| 2,224,464 | 12/1940 | Wolf | 606/45 |
| 3,955,578 | 3/1976 | Chamness | 606/47 |
| 5,078,716 | 1/1992 | Doll | 606/48 |
| 5,158,561 | 10/1992 | Rydell et al. | 606/49 |
| 5,201,741 | 4/1993 | Dulebohn | 606/45 |
| 5,207,686 | 5/1993 | Dolgin | 606/45 |

*Primary Examiner*—Stephen C. Pellegrino
*Assistant Examiner*—Michael Peffley
*Attorney, Agent, or Firm*—Frederick Gotha

[57] ABSTRACT

An electrosurgical selectively controllable loop electrode for laparoscopic surgery is set forth which includes a housing having a longitudinal axis and an axially extending cavity forming a passageway through the housing. A shaft member is slideably mounted to the housing within the cavity so as to permit axial and rotational displacement of the shaft member relative to the housing. A wire electrode which has a first end segment and a second end segment is in electrical communication with the shaft member and extends distally therefrom; the wire electrode also has a bridge segment integrally interconnecting the first and second end segments to form a loop. The end segments are biased by a pair of leaf springs of predetermined curvature where the springs are internally biased to open upon extension of the springs distally from the housing and to close upon external forces exerted against the springs by the housing during retraction. In another embodiment of the invention, the first and second end segments have a predetermined equilibrium shape and are self-biased to return to the equilibrium shape when displaced therefrom; the bridge segment integrally interconnecting the first and second end segments to form a loop is responsive to the internal restoring forces created when the bridge segment is displaced from equilibrium and the bridge segment articulates radially with respect to the end segments through a sequence of predetermined shapes.

9 Claims, 14 Drawing Sheets

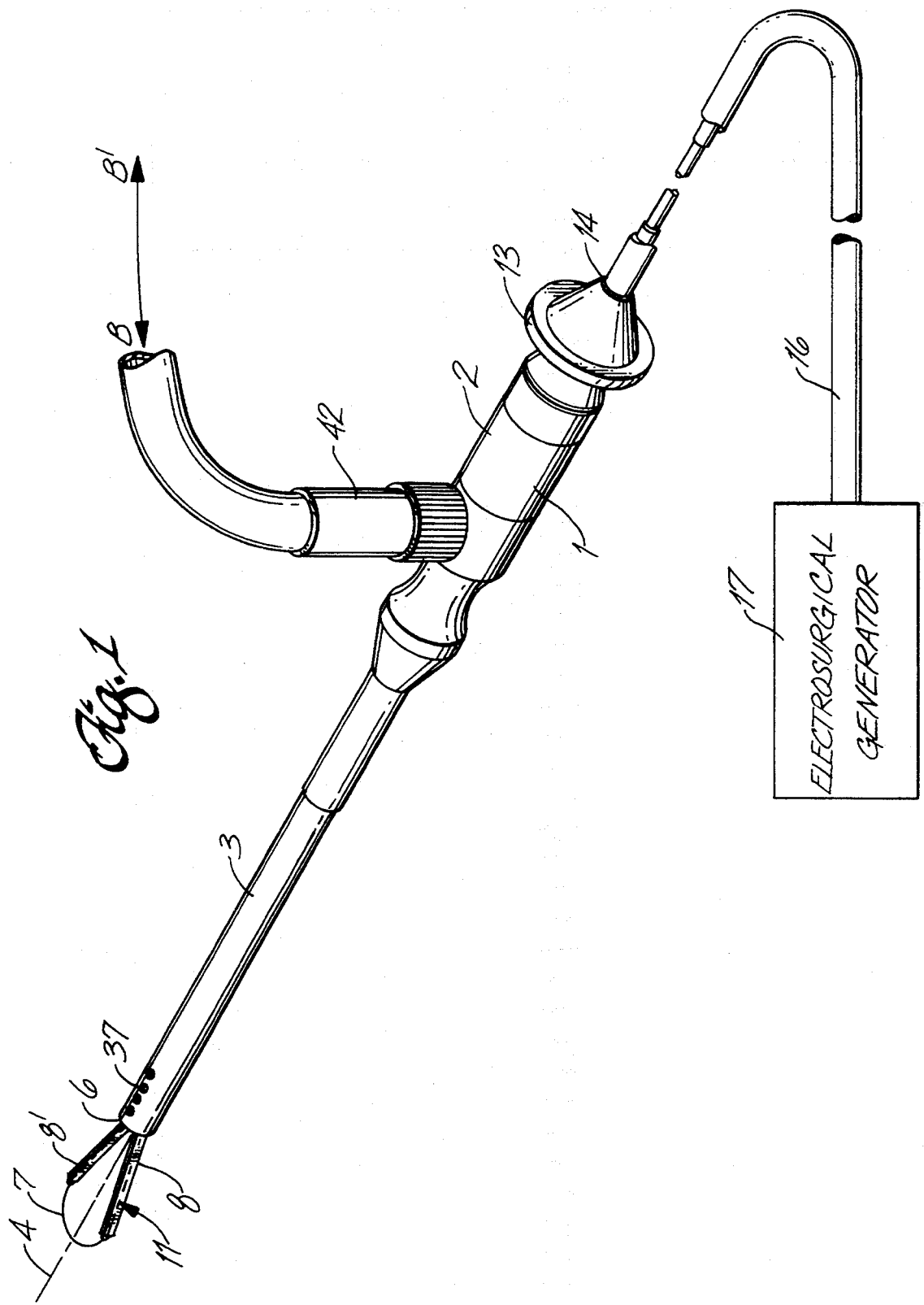

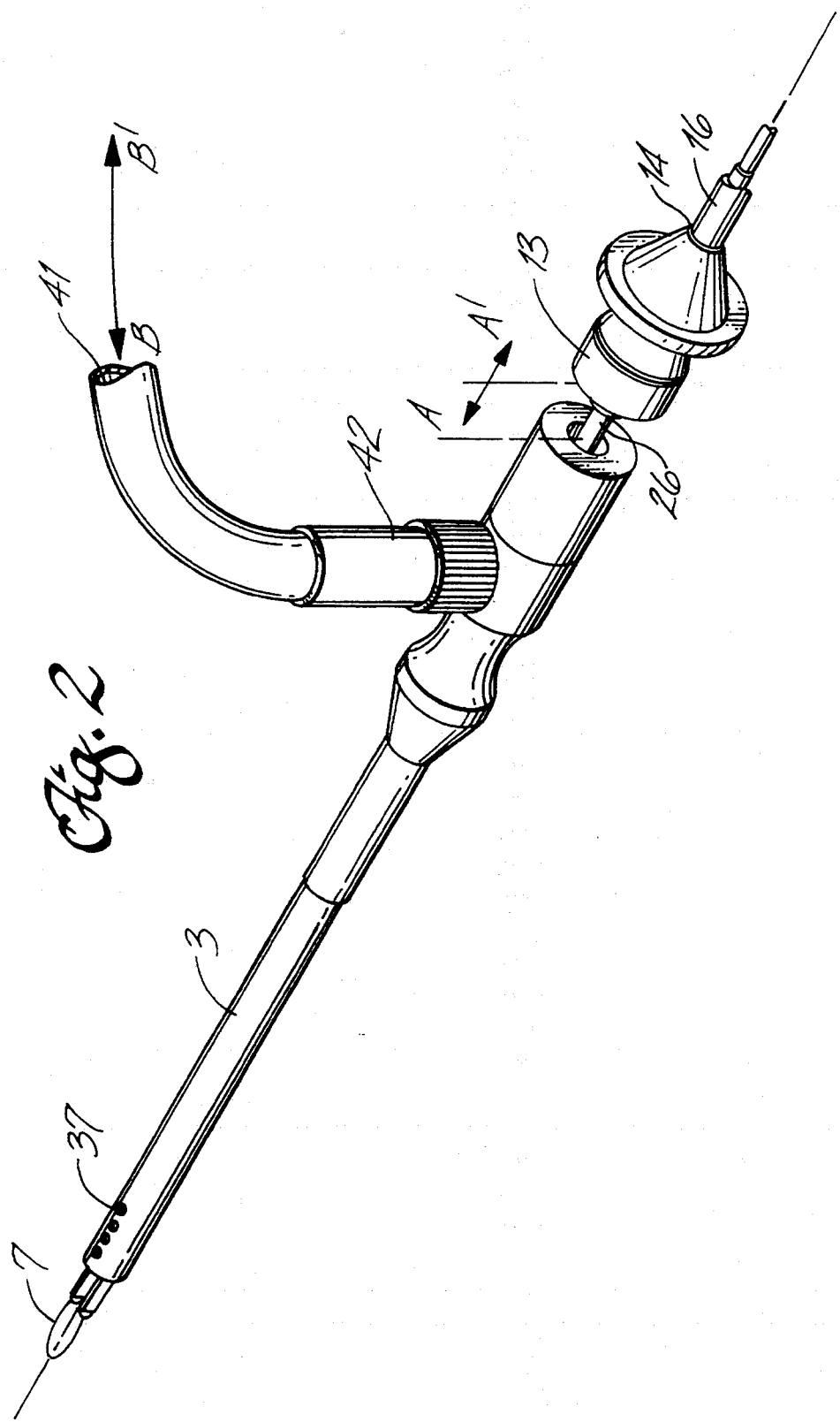

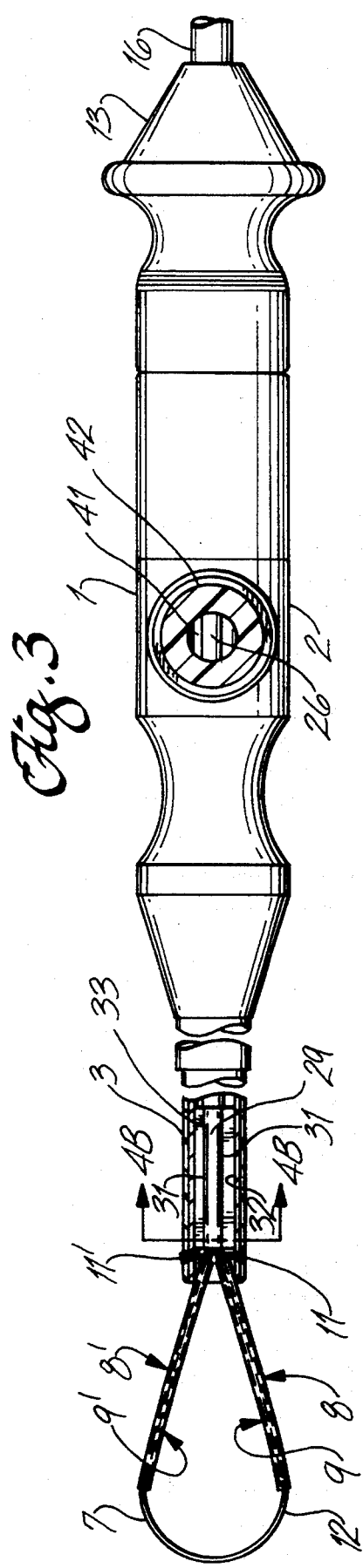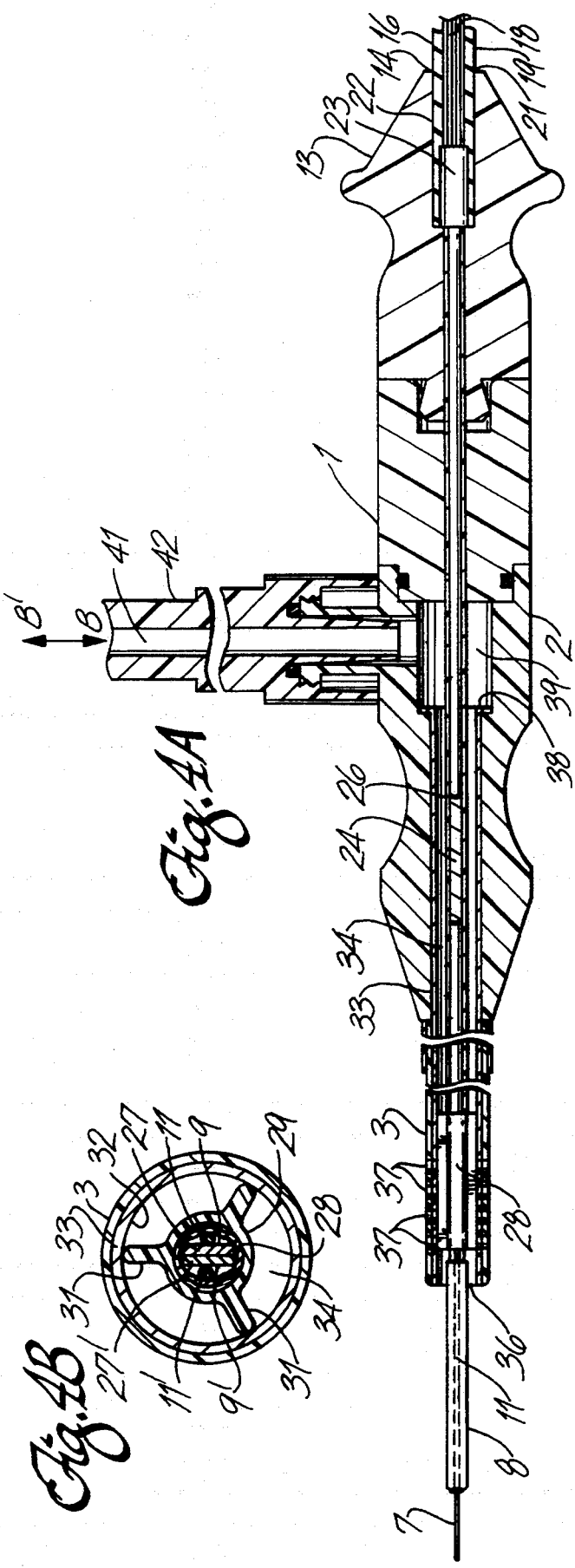

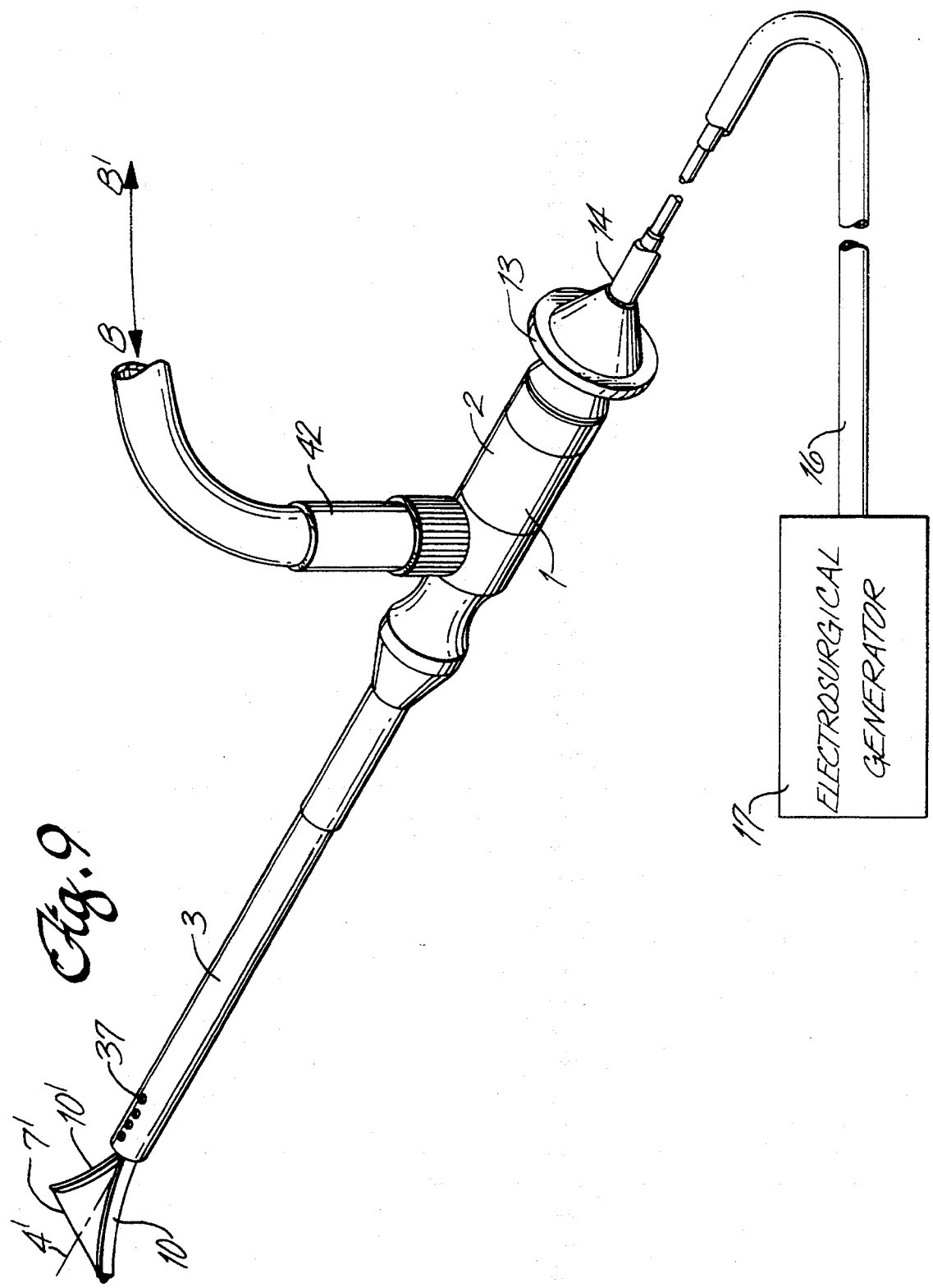

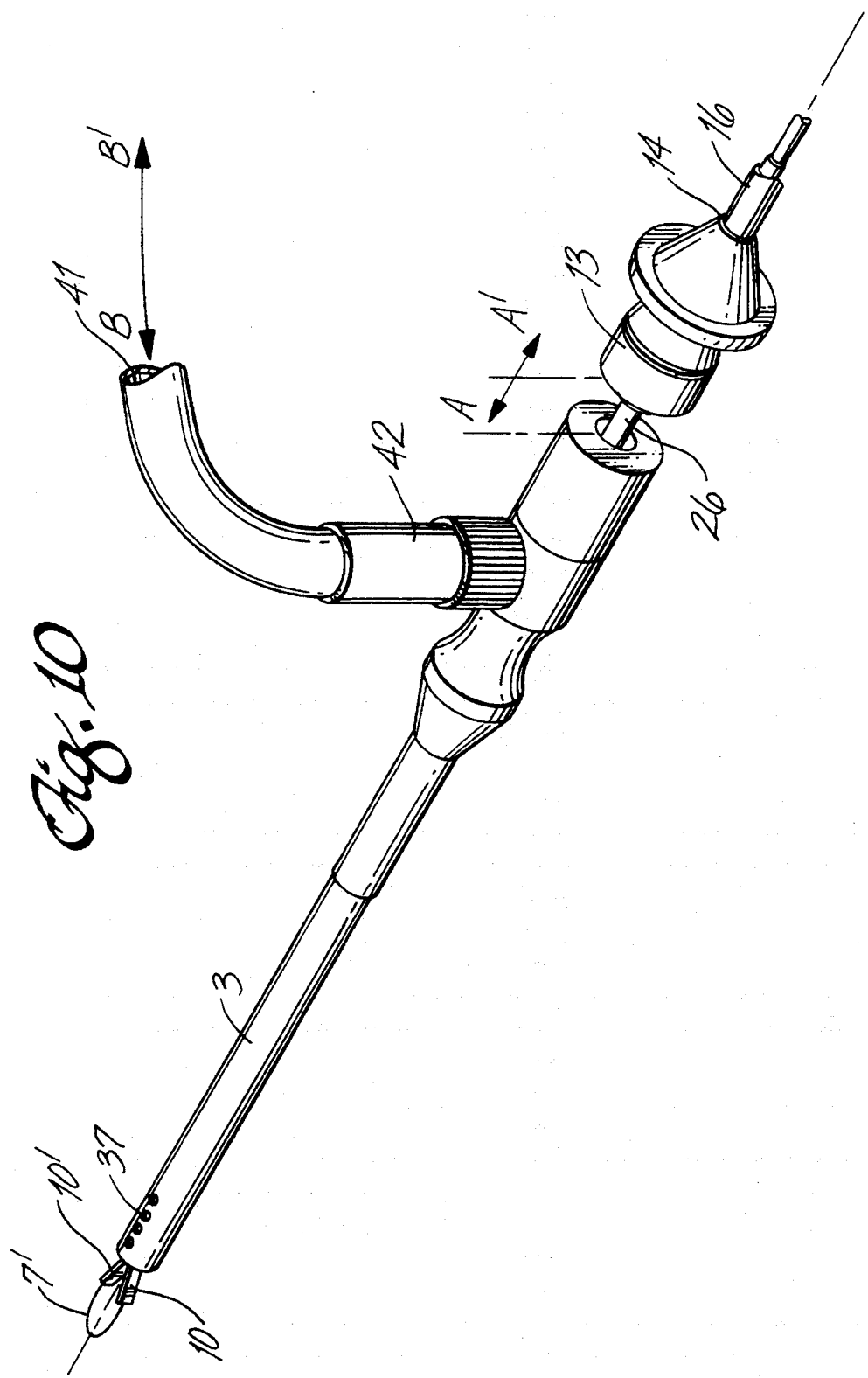

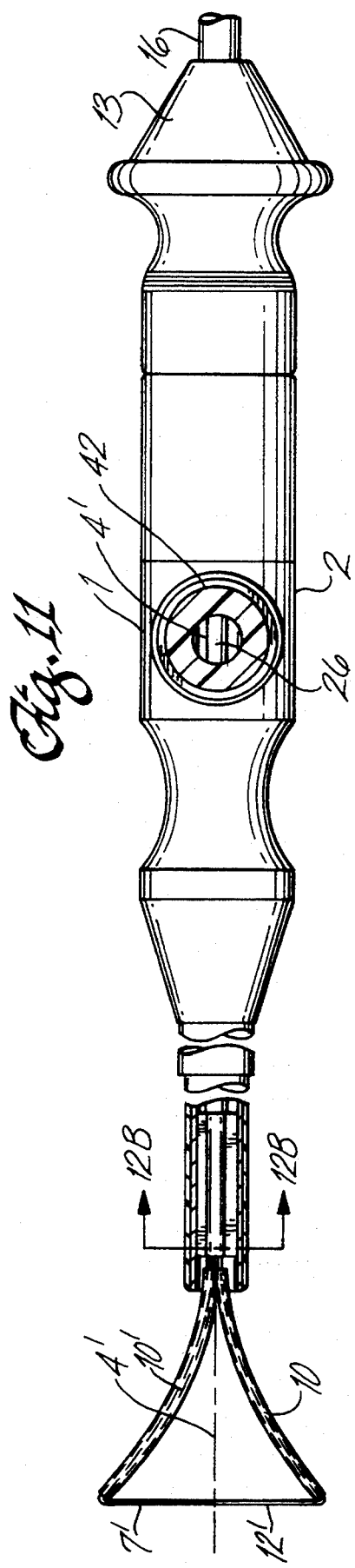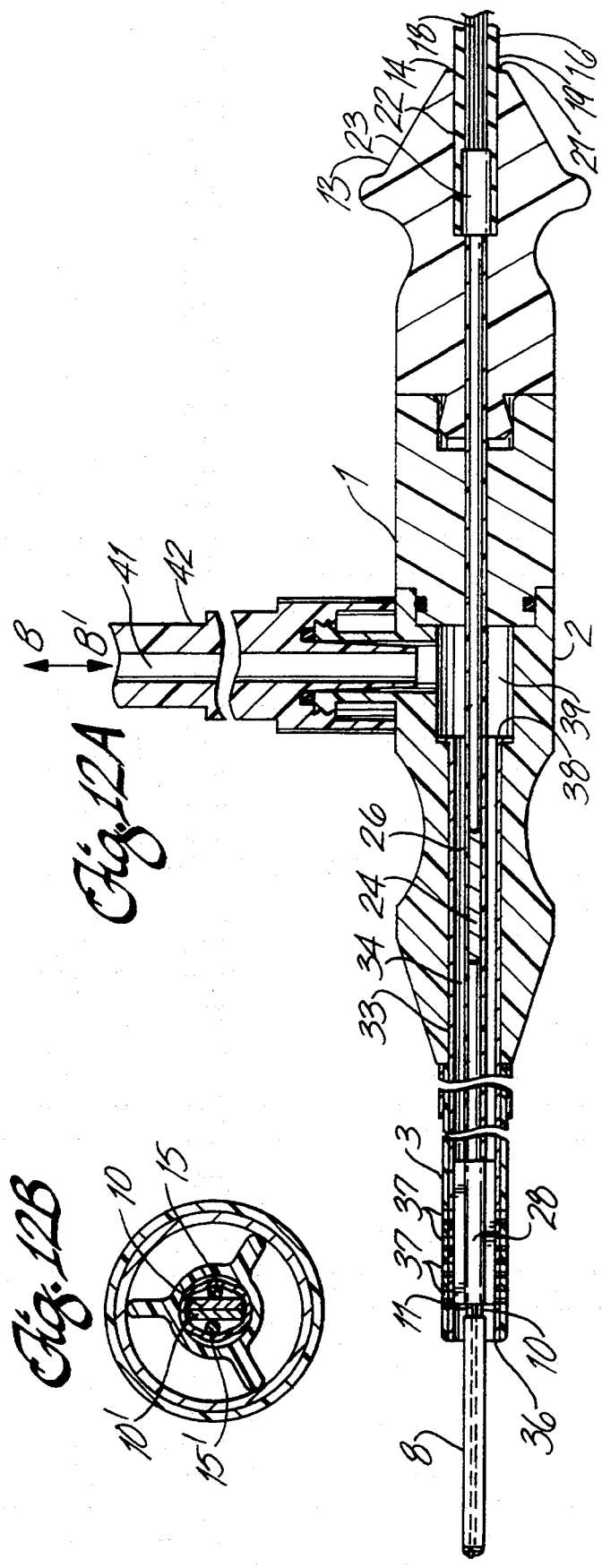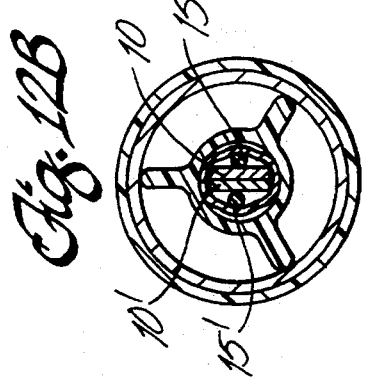

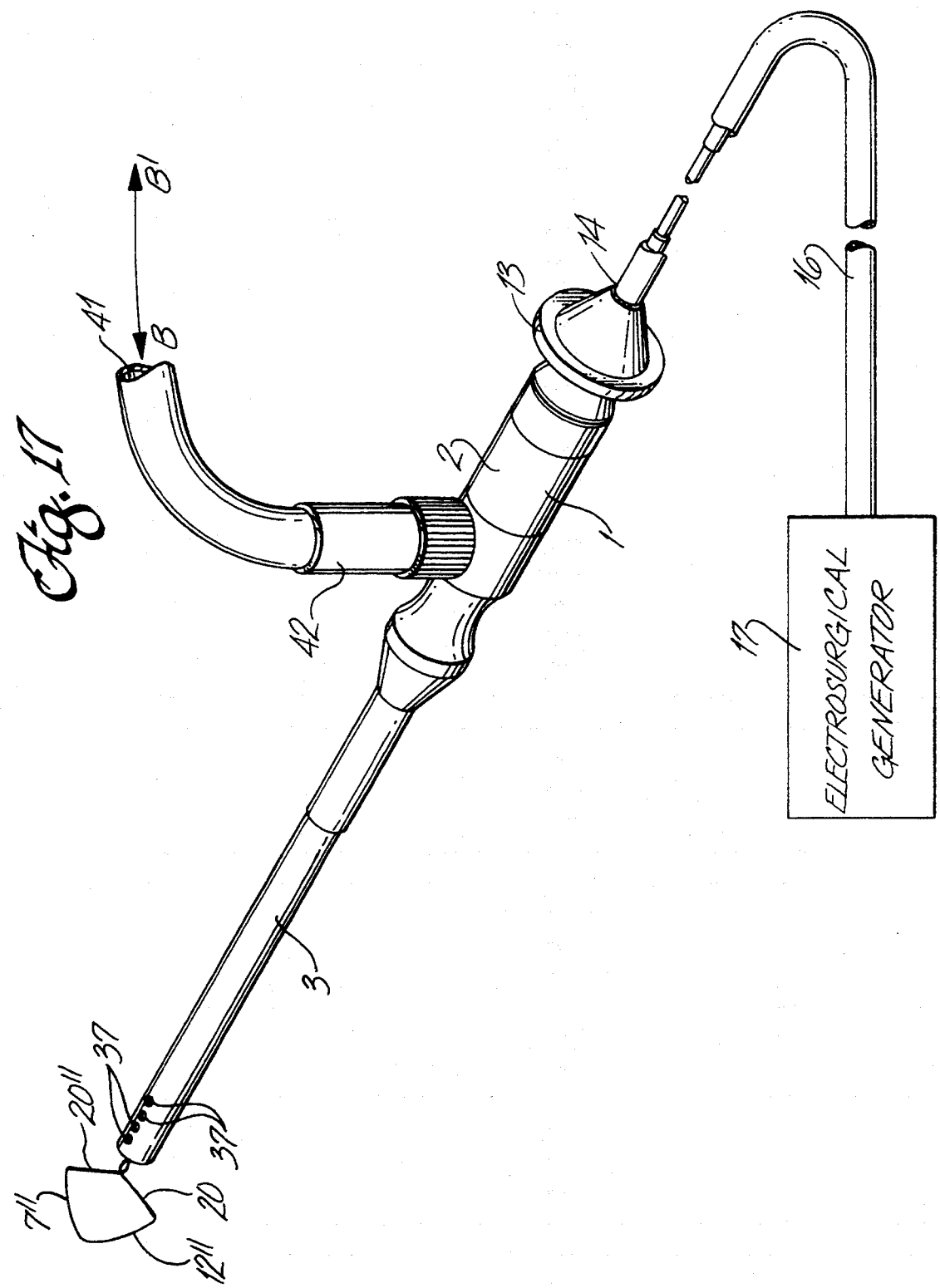

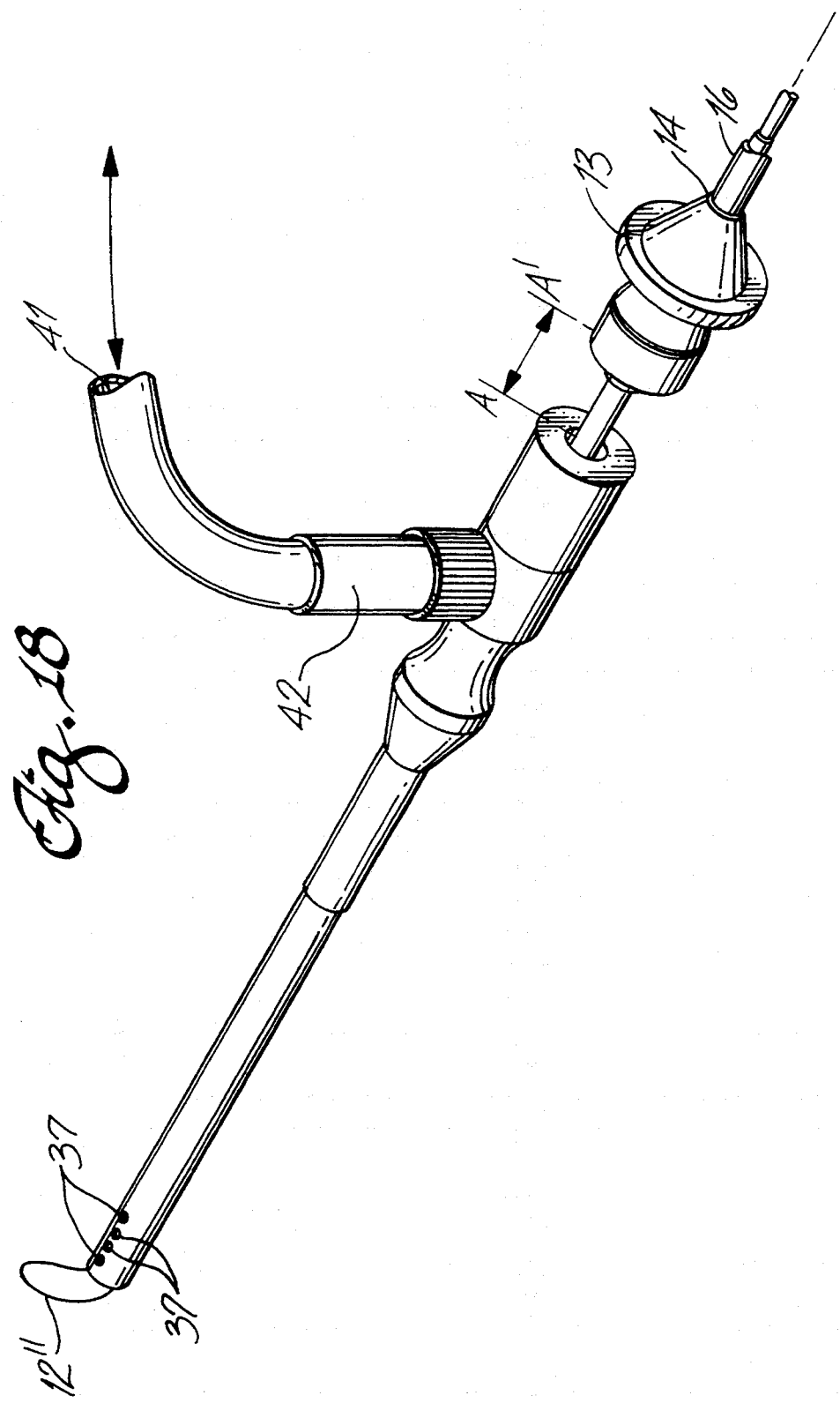

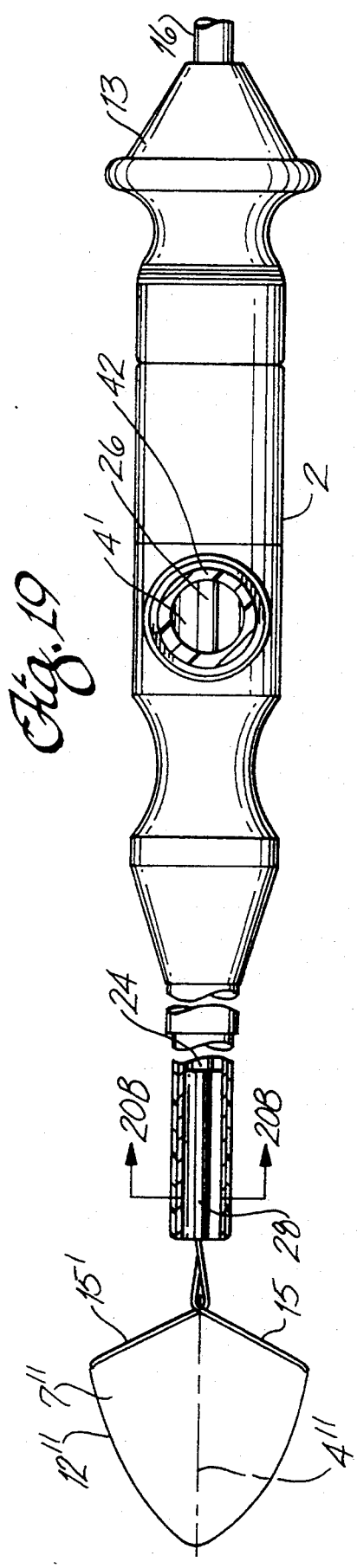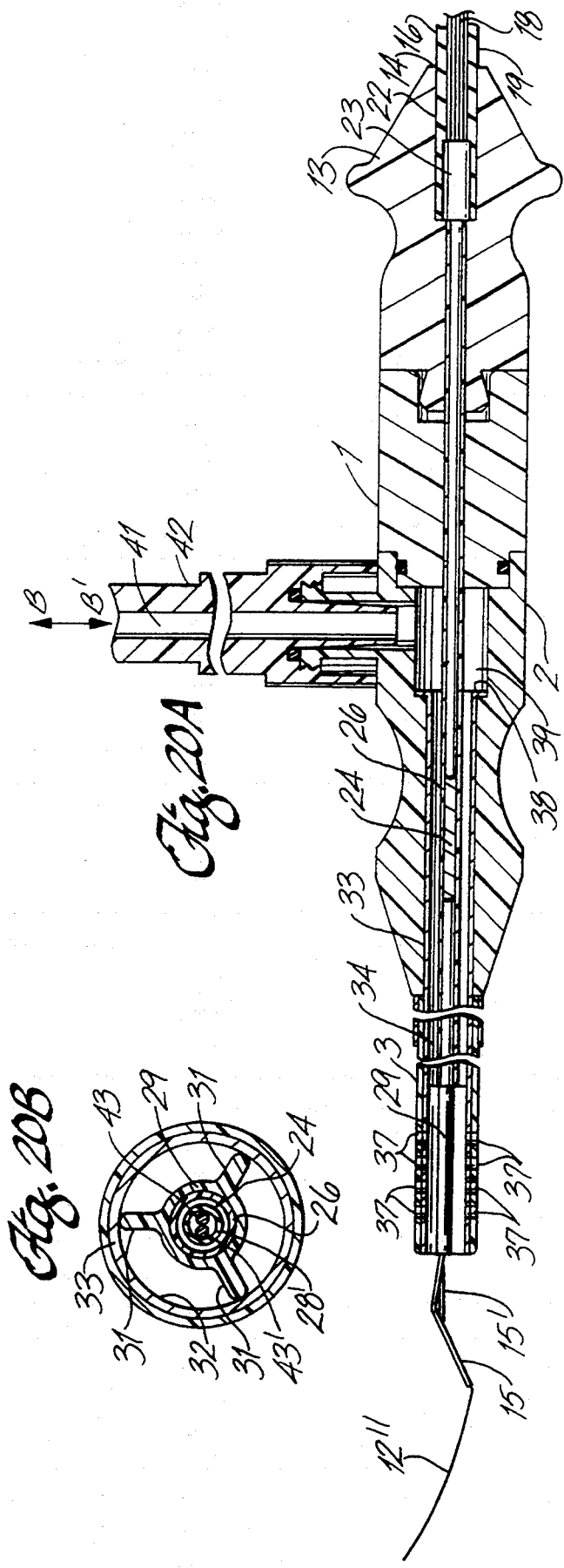

5,437,665

ELECTROSURGICAL LOOP ELECTRODE INSTRUMENT FOR LAPAROSCOPIC SURGERY

FIELD OF THE INVENTION

This invention relates to an electrosurgical loop electrode instrument for use in laparoscopic surgery for the excision of endometriosis, removal of leiomyomata, general biopsy, ovarian drilling or wedge resection, lapraoscopic uterosacral nerve ablation, cytoreduction of ovarian malignancy, and excision of the endometrium in the lower uterine segment following supracervical hysterectomy.

BACKGROUND OF THE INVENTION

Electrosurgical loops have been used most extensively in the prior art by urologists who use wire loops as components of electrosurgical resectoscopes to resect prostatic or bladder tumors endoscopically. Electrosurgical loops have also been employed through the use of the hysteroscope to resect leiomyomas, polyps, and in some cases the endometrium in patients who suffer from intractable bleeding disorders within the uterus.

Recently through the use of larger electrode loops, it has been demonstrated that it is possible to remove the transformation zones of the cervix affected with cervical intraepithelial neoplasis. Concerns that thermal damage secondary to electrosurgical technique would make the removed tissue difficult to evaluate from a histopathological perspective have been obviated by the development of new electrosurgical generators. The currents developed by these new generators combined with improvements in the design of the wire which comprises the loop, permit cervical specimens to be removed with minimal thermal damage and in many instances the thermal damage is less than that associated with $CO_2$ laser excision. The present state of the art, however, does not permit the use of electrosurgical loops during laparoscopic surgery within the peritoneal cavity. Currently available loop electrodes are inappropriate for laparoscopic surgery in that the fixed design of the electrodes make them impossible to use through the relatively small diameter laparoscopic ancillary cannulas. The use of electrosurgical loops, however, within the peritoneal cavity and under laparoscopic guidance would allow in many cases relatively simple and easy removal of endometriosis from a number of sites including the ovaries, the uterosacral ligament, the cul-de-sac and the pelvic sidewalls. The use of electrosurgical loop instrumentation presents enhanced enconomic benefits because the capital costs of electrosurgical loop instrumentation would be far less than that required for $CO_2$ or Nd-YAG laser-based procedures; additional economical benefits would also be achieved through low maintenance of the equipment and reduced training time of staff technicians and surgeons.

SUMMARY OF THE INVENTION

There is, therefore, provided according to the present invention, an electrosurgical loop electrode instrument for excising cervical tissue in an efficient and hemostatic fashion with minimal thermal damage. By selectively varying the region area enclosed by the loop, various sizes and depths of the loop are achievable; and thus the appropriate size of loop for resecting endometriosis from the surfaces of the ovaries or the parietal peritoneum or for removal of larger areas of endometriosis or for morcellation of myomas, ovaries or other masses may be selectively established.

The present invention is directed to an endoscopic electrosurgical electrode loop instrument for use in the peritoneal cavity for resecting endometriosis or for morcellation of myomas, ovaries or other masses. In one embodiment, the instrument is comprised of a housing having a longitudinal axis and an axially extending cavity through the housing and a metal shaft member which is in part insulated and slideably carried by the housing to permit both angular and axial displacement of the shaft relative to the housing. The shaft member at its distal end is in electrical communication with the first and second end segments of a continuous wire loop electrode which integrally interconnect to a bridge seqment forming a closed and continuous wire loop. A pair of leaf springs are oppositely and fixedly mounted to the distal end of the shaft member and are biased in a normally open position such that when the leaf springs are withdrawn into the housing by the shaft member, the leaf springs will be in a closed position and internally biased to spring apart upon emergence from the housing. The first and second end segments of the wire loop are securely held in bearing relationship with the leaf springs by first and second insulated sheaths such that the arcuate or bridge portion of the wire loop remains uninsulated. This permits current to flow into the patient who is at ground potential through the exposed portion of the bridge segment of the loop. Thus, by withdrawing the leaf springs into the housing the first and second end segments of the wire electrode laterally toward each other thereby reducing the radius of bridge segment of the wire loop. The withdrawal or extension of the shaft member into or from the housing, therefore, selectively permits the surgeon to choose the appropriate loop size for resecting or morcellating body tissue.

The housing is comprised of a handpiece and a distally extending insulated tube which has a plurality of orifices located adjacent its distal end for the introduction of irrigation fluid and also for the evacuation of vapor resulting from thermal resecting or morcellation of body tissue. A lumen for the introduction of irrigating fluid and for the evacuation of vapor or smoke communicates with a conduit cavity extending through the roundpiece and insulated outer tube thereby constituting a single flow path for evacuated and irrigating fluids.

In another embodiment of the invention, the loop electrode comprises a pair of oppositely mounted arcuate cantliever leaf springs which extend distally from the distal end of the shaft member with a convex curvature relative to the longitudinal axis respectively. A flexible bridge wire electrode interconnects and is in electrical communication with the distal ends of the cantliever springs which are at least in part insulated and in electrical communication with a metal shaft member slidably and rotationally mounted to a housing. When the cantliever springs are fully extended distally of the housing, the bridge wire interconnecting the springs has an infinite radius of curvature and extends laterally the longitudinal axis. Upon retraction of the cantliever springs into the housing, the springs close upon each other and the bridge wire radius sequentially decreases through collapsing concave loop configurations until fully withdrawn into the housing.

In yet another embodiment of this invention, an electrosurgical instrument is provided for selectively controlling the loop attitude of the electrode. This embodiment comprises a housing having a longitudinal axis and an axially extending cavity therethrough. A metal shaft member is slideably mounted within the cavity and adapted to permit axial and rotational displacement of the shaft relative to the housing. At the distal end of the shaft member, a continuous wire electrode loop has a first end segment and a second end segment where the first and second end segments are insulated and in electrical communication with the shaft member; an uninsulated bridge segment integrally interconnects the first and second segments forming a conductor for passage of current in the ground potential of the patient. The wire has a predetermined shape and is integrally biased such that external forces acting on the first and second segments by the inner wall of the metallic conduit of the housing during retraction of the wire into the housing collapses the loop through a sequence of predetermined shapes and upon extension of the wire from the housing, the loop expands through a sequence of predetermined shapes such that the attitude of the loop is selectively controllable.

BRIEF DESCRIPTION OF THE DRAWINGS

These and other features and advantages will become appreciated as the same become better understood with reference to the following specification, claims and drawings wherein:

FIG. 1 is a perspective view of one embodiment of the endoscopic electrosurgical loop electrode instrument of this invention.

FIG. 2 is a perpective view of the embodiment illustrated in FIG. 1 where the radius of the loop electrode is changed by withdrawal of the loop electrode into the housing.

FIG. 3 is a part cross-sectional top view of FIG. 1.

FIG. 4A is a left side cross-sectional elevational view of FIG. 3.

FIG. 4B is a cross-sectional view taken along the lines 4B—4B of FIG. 3.

FIG. 9 is a perspective view of another embodiment of the endoscopic electrosurgical loop electrode instrument of this invention.

FIG. 10 is a perpective view of the embodiment illustrated in FIG. 9 where the radius of the loop electrode is changed by withdrawal of the loop electrode into the housing.

FIG. 11 is a part cross-sectional top view of FIG. 9.

FIG. 12A is a left side cross-sectional elevational view of FIG. 11.

FIG. 12B is a cross-sectional view taken along the lines 12B—12B of FIG. 11.

FIG. 17 is a perspective view of yet another embodiment of the endoscopic electrosurgical loop electrode instrument of this invention.

FIG. 18 is a perpective view of the embodiment illustrated in FIG. 17 where the radius and attitude of the loop electrode is changed by withdrawal of the loop electrode into the housing.

FIG. 19 is a part cross-sectional top view of FIG. 17.

FIG. 20A is a left side cross-sectional elevational view of FIG. 19.

FIG. 20B is a cross-sectional view taken along the lines 20B-02B of FIG. 19.

FIGS. 27a-27d illustrate the use of the electrosurgical loop electrode to resect tissue.

DETAILED DESCRIPTION

Figure 5:
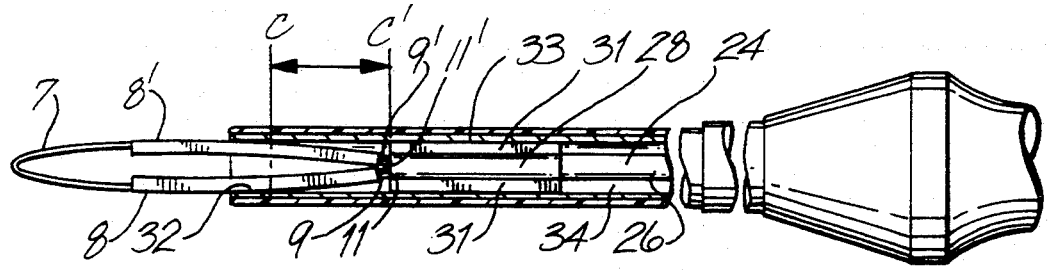
FIG. 5 is a part cross-sectional top view of FIG. 2 illustrating the collapsability of the loop electrode.

FIG. 1 illustrates in a perspective view, one embodiment of the electrosurgical loop electrode instrument of this invention. The instrument is shown in FIG. 1 in a fully extended open position. In order to introduce the loop electrode into the operative region of the patient, the distal end of the instrument must be inserted through a trocar or canulla to gain access to the operative region. The trocars or canullas used in laparoscopic surgery for access to the peritoneal cavity generally have an inside diameters of 5 mm or 10 mm. As can be seen in FIG. 1, the loop electrode when fully extended has a radius which exceeds that of the distal end of the instrument thereby requiring that the loop be withdrawn into the instrument before insertion through the trocar to reach the operative region.

Referring again to FIG. 1, an electrosurgical loop electrode instrument is shown having a housing 1 which is comprised of a handpiece 2 and an insulating outer tube 3. As can be seen in FIG. 1, the housing 1 is generally symmetrical about longitudinal axis 4. At the distal end 6 of the insulated outer tube a wire electrode 7 extends continuously and is in part disposed within a pair of spring insulation sheaths 8 and 8'. As can more clearly be seen in FIG. 3, a pair of internally biased flat leaf springs 9 and 9' are oppositely spaced from each other laterally of the longitudinal axis of the housing and are at least in part also disposed in and enclosed by sheaths 8 and 8'. The wire electrode 7 has a first end segment 11 and a second end segment 11' which extend through sheaths 8 and 8' respectively and are integrally connected by bridge segment 12 forming a continuous closed wire loop.

FIG. 2 illustrates the withdrawal of the wire electrode 7 into insulated tube 3. As can be see in FIG. 2 as the leaf springs 9 and 9' are laterally collapsed during retraction into insulated outer tube 3, the radius of the bridge segment 12 of the wire loop decreases which changes the curvature of the loop electrode and consequently the cutting angle of the wire. As can further be seen in FIG. 2, the housing comprises an adjustment member 13 which has an opening at its proximate end 14 for receipt of the connector 16 from the electrosurgical generator 17. By referring to FIG. 4A, the adjustment member 13 can be seen in cross-section and the electrical connection extending axially between the connector 16 and the wire 7 demonstrated along with the internal structure of the housing. The connector 16, as can be seen in FIG. 4A, has an internal wire 18 which is surrounded by insulation 19 and passes through the opening 14 located at the proximate end 21 of the adjustment member 13. Longitudinally extending cylindrical cavity 22 communicates with the opening 14 for receipt of connector 16; the connector 16 is in fixed relationship with the adjustment member 13 within cavity 22 which precludes any relative axial displacement between them. Proceeding distally from the proximate end 21 of adjustment member 13, it can be seen that internal wire 18 is fixed in electrical communication with conducting member 23 which in turn is in electrical communication with an axially extending metal shaft 24 surrounded by an insulating material 26. The insulating material is integral with the metal shaft and upon proximate axial displacement of the adjustment member 13, metal shaft 24 may be displaced axially relative to the housing so as to withdraw wire electrode 7 proximately and sequentially into insulated outer tube 3. The movement axially of adjustment member 13 is illustrated by the arrow A-A' shown in FIG. 2.

Continuing with the electrical communication between the metal shaft 24 and the wire electrode 7, reference is made to FIGS. 3, 4A and 4B. FIG. 4B is a cross-sectional view taken along the line 4B—4B of FIG. 3 and as can be seen in FIG. 4B, the proximate ends 27 and 27' of leaf springs 9 and 9' are in contact with the first and second end segments 11 and 11' respectively of the wire electrode 7. A casing 28 made of a conductive material is in electrical communication with both the metal shaft 24 and the first end and second end segments 11 and 11'. The proximate ends of leaf springs 9 and 9' are in fixed relationship with metal tube 24 and thus axial displacement of the metal tube 24 will result in a like displacement of the leaf springs 9 and 9'. A spacer member 29 which is made of an insulated material encloses the casing 28 and has spacer prongs 31 extending radially therefrom which are in slideable and rotational contact with the inner wall 32 of metallic conduit 33. Referring now to FIG. 4A, it can be seen that metallic conduit 33 extends axially within housing 1 and at its distal end is surrounded by insulated outer tube 3. Thus, spacer member 29 maintains metal shaft 24 substantially centered within conduit cavity 34 of metallic conduit 33. Conduit cavity 34 permits the introduction of irrigating fluid into the operative region of the patient through distal opening 36 and also the evacuation of vapor or smoke.

Evacuation of vapor from the operative region occurs through distal opening 36 and the plurality of orifices 37 which are contained in the distal end of insulated outer tube 3. These orifices extend through metallic conduit 33 to communicate with the conduit cavity 34. The proximate end 38 of metallic conduit 33 communicates with chamber 39 which in turn communicates with the lumen 41 of fluid connector 42. Line B-B' shown in FIGS. 1, 2 and 4A illustrates that the fluid flow through the passageway comprising metallic conduit 33, chamber 39 and lumen 41 is bidirectional, i.e., a single flow path for both irrigation and evacuation of fluid.

FIG. 5 represents a top view of the electrosurgical loop electrode instrument with the wire electrode 7 partially withdrawn into conduit cavity 34. Spring members 9 and 9' are insulated by sheaths 8 and 8' and as the wire electrode is withdrawn into metallic conduit 33 through distal opening 36, the leaf springs are collapsed laterally towards each other and the radius of the bridge segment 12 of wire electrode 7 is sequentially reduced until the leaf springs have been collapsed a maximum distance laterally by the force exerted against them by the inner wall 32 of metallic conduit 33.

Figure 6:
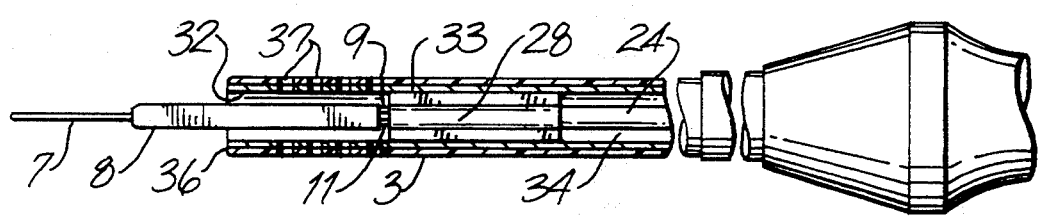
FIG. 6 is a partial cross-sectional left elevational side view of FIG. 5.
Figure 7:
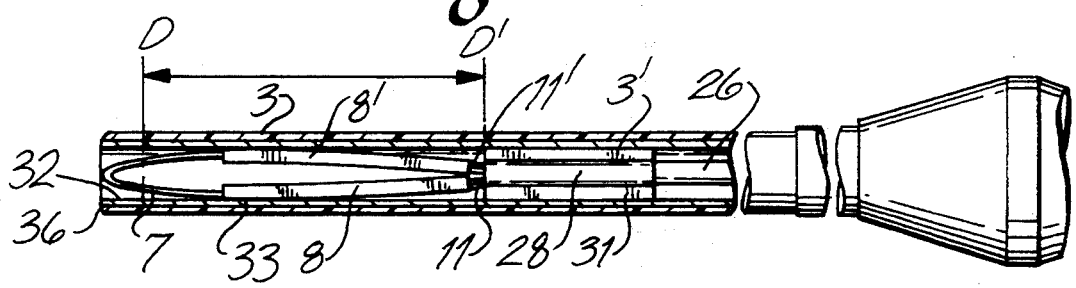
FIG. 7 is a partial cross-sectional view of FIG. 5 illustrating the complete retraction of the loop electrode into the housing.
Figure 8:
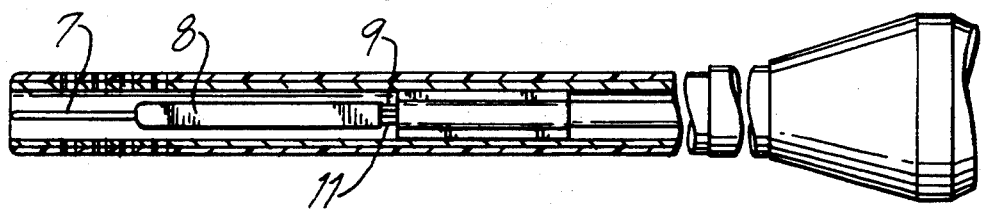
FIG. 8 is a left side elevation cross-sectional view of FIG. 7.

A left side-elevational view of FIG. 5 is shown in FIG. 6 illustrating the wire electrode partially withdrawn into the housing. The bidirectional arrows CC' shown in FIG. 5 illustrate the axial displacement of metal shaft 24. As can be seen in FIG. 5, metal shaft 24 is surrounded at least in part by insulation 26. Complete retraction of the loop electrode 7 into the conduit cavity 34 is show in FIGS. 7 and 8 where FIGS. 7 is a top view of the instrument and FIG. 8 is a left elevational side view in partial cross-section. The bidirectional arrow DD' shown in FIG. 7 illustrates the axial displacement of metal shaft 24 and the complete retraction of the wire electrode into the housing. Thus, an embodiment of this invetion has been shown of an electrosurgical loop electrode instrument for use in laparoscopic surgery where the wire electrode 7, by withdrawal or extension of an insulated internal metal shaft, may be varied in radius thereby allowing the surgeon to conveniently vary the cutting radius of the wire electrode to perform a resection or removal of endometriosis or for morcellation of myomas, ovaries or other masses.

Another embodiment of this invention is shown in FIGS. 9 through 16. In this embodiment of the invention, the instrument housing is identical to the housing 1 illustrated in FIGS. 1, 2,3 4A and 4B. Referring, however, to FIG. 11, it can be seen that at the distal end of the housing when the loop electrode is fully extended, the bridge segment 12' of loop electrode 7' is substantially perpendicular to the longitudinal axis 4' of the instrument. In this embodiment of the invention, the leaf springs 10 and 10' are internally biased such that when the springs are fully extended from the housing their curvature is convex with respect to longitudinal axis 4'. Thus, upon extension from the housing the distal ends of the leaf springs will be laterally spaced from each other at a greater distance than in the embodiment shown in FIGS. 1 through 8. The wire electrode 7' therefore extends vertically and is substantially perpendicular to the longitudinal axis presenting an increased loop radius for the removal of endometriosis or morcellation of myomas, ovaries or other masses.

Figure 13:
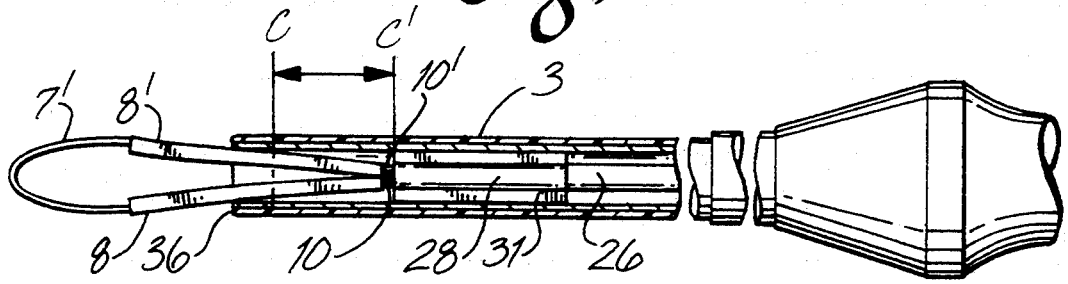
FIG. 13 is a part cross-sectional top view of FIG. 10 illustrating the collapsability of the loop electrode.
Figure 14:
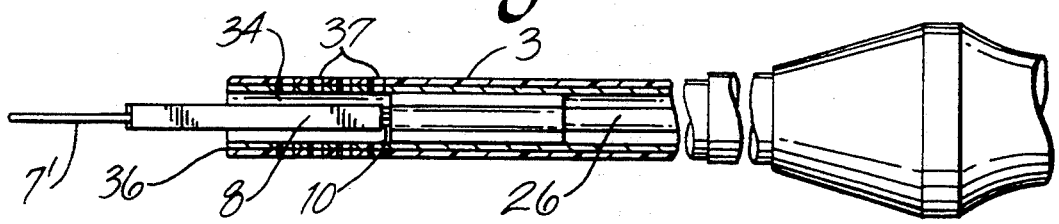
FIG. 14 is a partial cross-sectional left elevational side view of FIG. 13.
Figure 15:
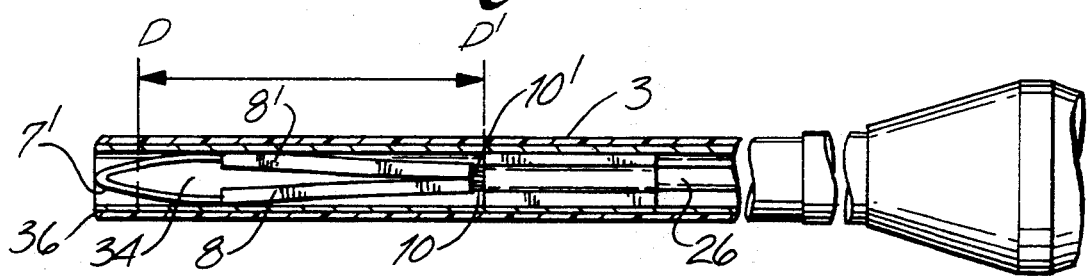
FIG. 15 is a partial cross-sectional view of FIG. 10 illustrating the complete retraction of the loop electrode into the housing.
Figure 16:
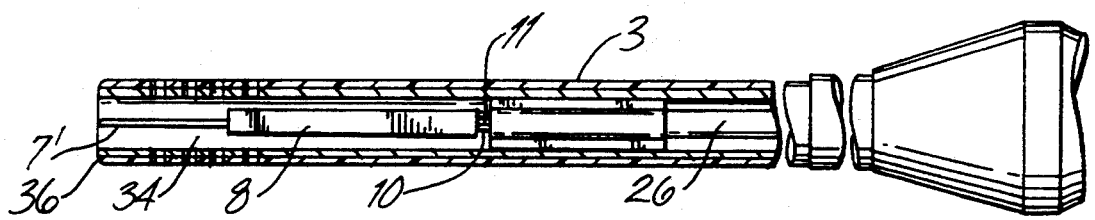
FIG. 16 is a left side elevation cross-sectional view of FIG. 15.

FIGS. 13, 14, 15 and 16 illustrate the withdrawal of wire loop 7' into the housing 1 and it can be seen in FIG. 13 that because of the convex internally biased shape of leaf springs 10 and 10', that upon withdrawal through distal opening 36 into the housing, a larger loop radius of wire electrode 7' is permitted as compared to the radius of loop electrode 7 in FIG. 5. Thus, through the utilization of internally biased convex leaf springs 10 and 10', larger loop diameters are permitted for resection and morcellation. FIG. 14 is a left elevational side view in part cross-sectional view of FIG. 13 and shows the partial withdrawal of electrode 7' into conduit cavity 34. By referring to FIGS. 15 and 16, the complete withdrawal or retraction of loop electrode 7' into the housing is illustrated. It is in this configuration that the electrode is introduced into the operative region of the body by passage through the trocar or cannula (not shown) after which by axial displacement of axially extending metal shaft 24 loop electrode 7' may be sequentially opened and in its fully opened position, present an infinite radius of curvature for maximizing the morcellation of myomas, ovaries or other body masses.

Referring to FIG. 12B, which is a cross-section in the direction of line 12B—12B shown on FIG. 11, it can be seen that the first and second end segments, respectively, 15 and 15' are in contact with the proximate ends 10 and 10' respectively of the leaf springs. The springs in turn are in electrical communication with metal shaft 24 thereby placing the loop electrode 7' in electrical communication with electrosurgical generator 17. Although not shown in the figures of this invention, but well known in the prior art, the electrosurgical generator may be selectively energerized to permit current to flow from the generator, to the loop and into the patient's body which is grounded. The heat generated by the flow of current into the body is of sufficient intensity to permit resection or morcellation of body tissue. Since cutting occurs where the wire electrode is in contact with the body, the ability to change the radius of the cutting loop during laparoscopic surgery is of great advantage. It is also advantageous to have an electrosurgical loop electrode where the attitude of the loop can be varied during laparoscopic surgery by the surgeon to facilitate access to tissue which is to be resected or morcellated during the surgery. An instrument to permit such controllable loop attitude is yet another embodiment of this invention and is described hereafter.

Another embodiment of this invention is shown in FIG. 17. The structure of the housing in FIG. 17 is identical to the housing described above in the first two embodiments of this invention; however, the embodiment described hereinafter contains a loop electrode which has a predetermined or "memorized" shape and is self-biased such that external forces exerted on the first and second segments by insulated metallic conduit 33 during retraction of the wire into the housing collapses the loop through a sequence of predetermined shapes which permits the surgeon to selectively change the attitude of the loop during laparoscopic surgery by axial extension or retraction of metal shaft member 24. FIG. 17 illustrates the loop electrode in a fully extended positions which represents the equibirum position or "remember" shape of the metal loop alloy. Referring again to FIG. 17, the wire electrode 7" has first and second segments 20 and 20' which are insulated and integrally connected to bridge segment 12" of the wire electrode. As can be seen in FIG. 18, as the wire electrode is withdrawn into the housing, first and second end segments 20 and 20' sequentially collapse resulting in a sequential change in the shape and attitude of the bridge segment 12" of the wire electrode. As can be seen by comparing FIG. 17 and FIG. 18, the attitude of the wire loop in FIG. 18 has shifted approximately 90 degrees from the attitude of the loop as shown in FIG. 17.

The axially extending metal shaft 24 is in electrical communication with wire loop 7" which is illustrated in FIGS. 19, 20A and 20B. Shaft member 24 is slideably mounted within the housing and may be displaced axially and rotationally within the housing by movement of adjustment member 13 or axially to achieve the axial displacement or rotationally to rotate metal shaft 24 within the housing. Thus, the structure of the instrument permits not only the attitude change of the bridge segment 12" as the wire electrode 7" is withdrawn from the housing but also permits the surgeon to rotate wire electrode 7" thereby omnidirectionally controlling the position and attitude of the looped bridge segment 12".

By referring to FIGS. 19 and 20B, it can be seen that wire electrode 7" has a predetermined shape in its fully extended or equibirum position from the housing where the first and second end segments 15 and 15' laterally intersect the longitudinal axis 4" in an overlapping configuration and thereafter have abrupt changes in slope or direction and then again intersect the longitudinal axis 4" intermediate the distal end of the housing and the first intersection of end segments 15 and 15'. The proximate ends 43 and 43' of end segments 15 and 15' are shown in cross-section in FIG. 20B. Proximate ends 43 and 43' are in electrical communication with axially extending metal shaft 24. Referring again to FIG. 20B, it can be seen that proximate ends 43 and 43' are incased by insulated casing 28' which is crimped to metal shaft 24. Spacer member 29 through spacer prongs 31 which extend radially from spacer member 29, is in slideable and rotational contact with the inner wall 32 of metallic conduit 33. Thus, as in the previous embodiments, rotation of metal shaft 24 will rotate spacer member 29 within conduit cavity 34 which permits bridge segment 12" of wire electrode 7" to be rotated through 360 degrees.

Figure 21:
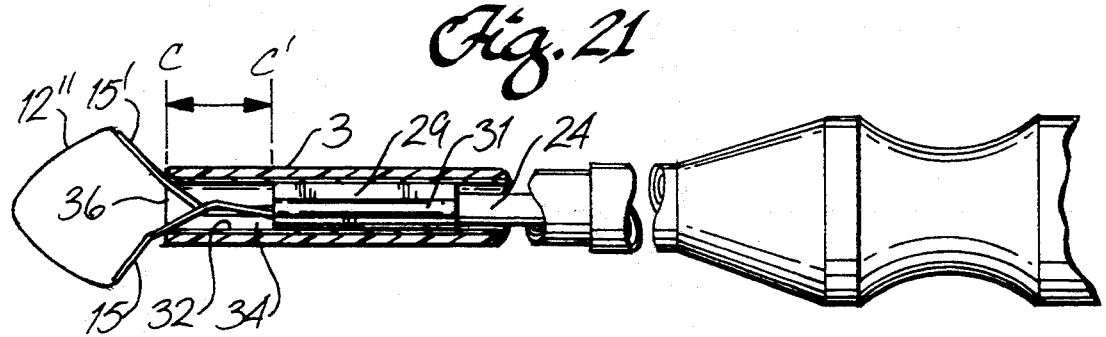
FIG. 21 is a part cross-sectional top view of FIG. 18 illustrating the collapsability of the loop electrode.
Figure 22:
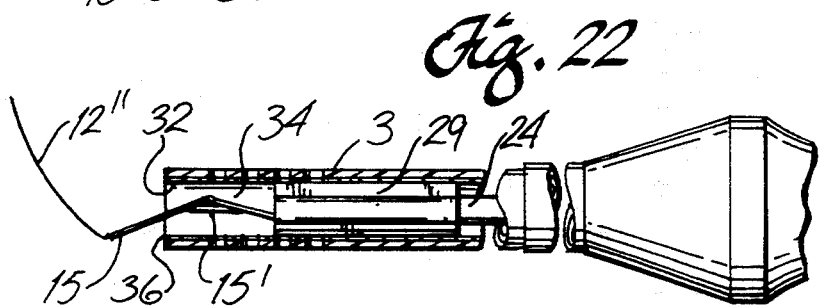
FIG. 22 is a partial cross-sectional left elevational side view of FIG. 21.
Figure 23:
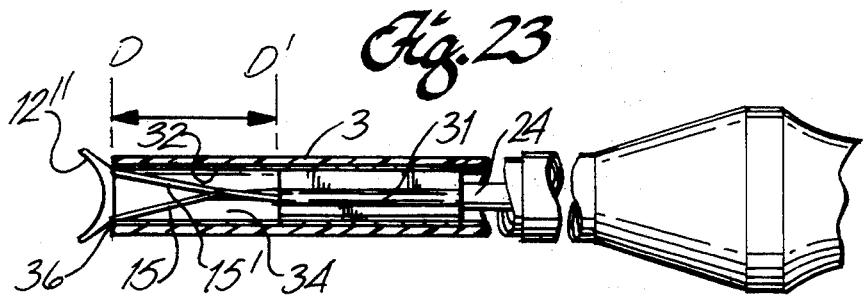
FIG. 23 is a top partial cross-sectional view of FIG. 18 illustrating the electrosurgical loop at a sequential stage during withdrawal into the housing.
Figure 24:
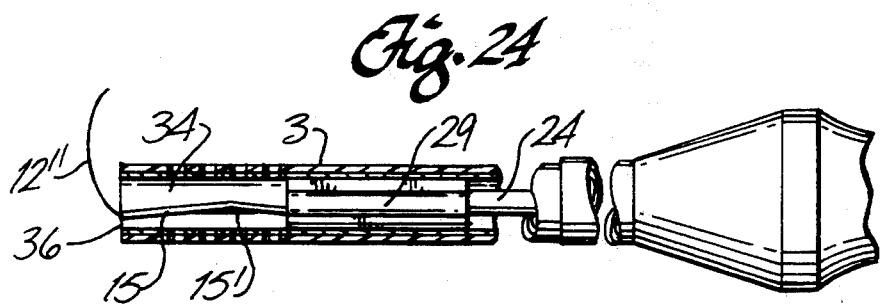
FIG. 24 is a part cross-sectional side view of FIG. 23.
Figure 25:
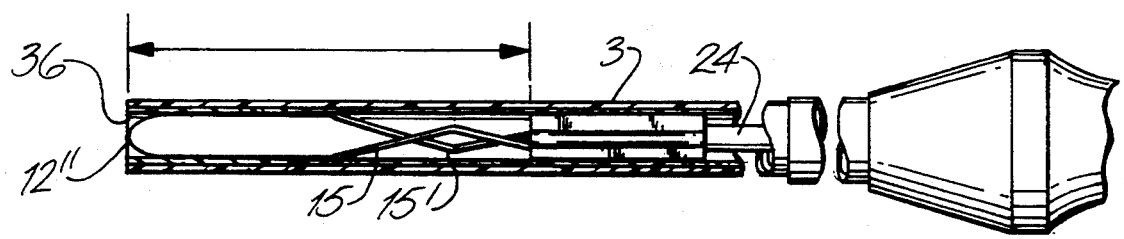
FIG. 25 is a part cross-sectional top view illustrating the electrosurgical loop of this embodiment of the invention retracted within the housing.
Figure 26:
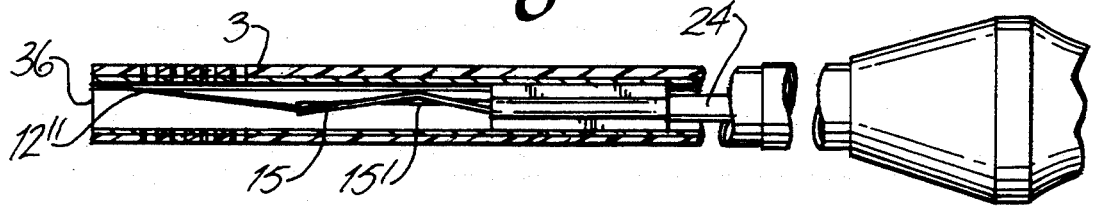
FIG. 26 illustrates a sequence of the resection of body tissue using the loop electrode shown in FIG. 17.

FIGS. 21, 22, 23, 24, 25 and 16 illustrate the attitude change of bridge segment 12" as the first and second end segments 15 and 15' of wire loop electrode 7" are withdrawn into the housing. As can be seen in FIGS. 22 and 24, as the wire electrode proceeds proximately into the housing the attitude of bridge segment 12" articulates toward the vertical. Likewise, as can be seen in FIGS. 21 and 23, which are top views of the wire electrode, illustrating the shape of the electrode changes as it sequentially is withdrawn into the housing. The configuration of the loop electrode after complete retraction into the housing is shown in FIG. 25 in a partial cross-sectional view and FIG. 26 illustrates a left side view of FIG. 25 in partial cross-section.

Figure 27A:
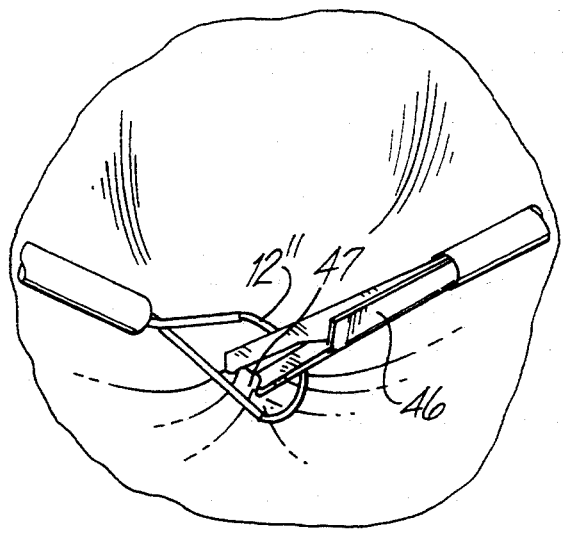
Figure 27B:
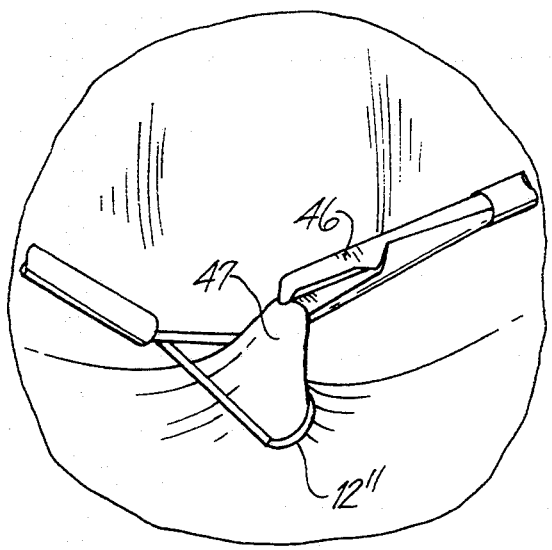
Figure 27C:
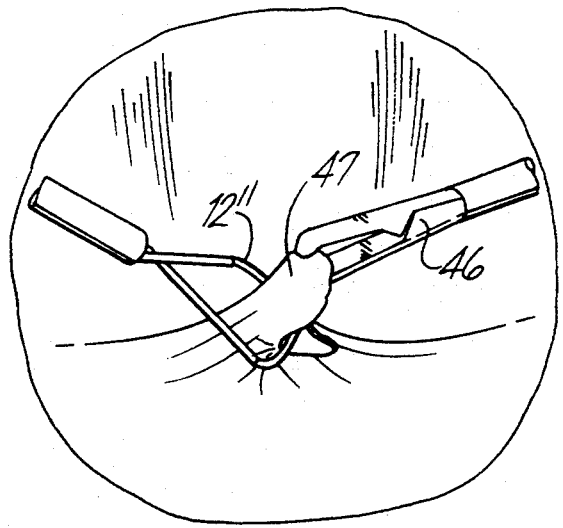
Figure 27B:
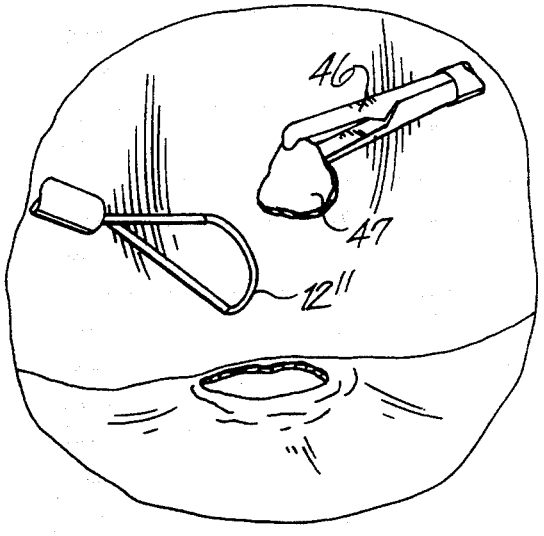

FIGS. 27A, B, C & D illustrate the use of the electrosurgical loop electrode to resect tissue. As can be seen in the Figures, a grasper tool 46 is introduced through a trocar or cannula into the operative region and is positioned within the wire loop to grasp the segment of body tissue 47 and lift it through the enclosed loop region. Thereafter the electrosurgical generator is selectively activated to permit current to flow into the loop and into the patient's body which is at a ground potential. Although not shown, a valve means communicating with lumen 41 for selectively providing either irrigating fluid or evacuating the vapor or smoke generated during the cutting process, is interposed between fluid connector 42 and a suction/irrigation pump.

The preferred materials for use in the wire loop electrode of the loop controllable attitude are materials which permit the wire electrode to be pre-formed and to have the property of being self-biased to bias the wire to return to its equibirum position. Alloy blends of Titanium and alloy blends of stainless steel are presently available and possess the physical properties to permit the loop electrode during withdrawal or retraction into the housing to proceed through a sequence of predetermined shapes resulting from the internal bias of the wire; likewise, upon extension of the loop electrode from the housing, the loop electrode will proceed through the sequential shapes and attitude changes until it is fully extended to its equibilirum position. Other alloy blends having the physical property above-described wouldbe suitable also as electrode loops.

While I have shown and described certain embodiments of the present electrosurgical loop electrode instrument for laparoscopic use, it is to be understood that these emodiments are subject to many modifications without departing from the scope and spirit of the claims as recited herein.

What is claimed is:

1. An electrosurgical instrument for selectively controlling the attitude of a loop electrode during laparoscopic surgery comprising:
   (a) a housing having a longitudinal axis, a proximate and distal end, and an axially extending cavity forming a passageway therethrough;
   (b) a shaft member having a proximate and distal end carried by said housing and slideably mounted within said cavity to permit axial and rotational displacement of said shaft member relative to said housing;
   (c) a wire electrode having a first end segment and a second end segment where said first and second end segments have distal and proximate ends and said proximate ends are in electrical communication with said shaft member, said first and second end segments having a predetermined equilibrium shape when said first and second end segments are not in bearing engagement with said housing, and where said first and second end segments are resiliently self-biased to return to said equilibrium shape when said distal ends of said first and second end segments are laterally displaced by bearing engagement of said first and second end segments with said housing, said wire further having a bridge segment integrally interconnecting said distal ends of said first and second end segments forming a loop and where the vertical attitude with respect to said lateral displacement and the shape of said bridge segment are contemporaneously responsive to said lateral displacement such that upon sequential lateral displacement of said distal ends of said first and second end segments from said equilibrium shape the attitude of said bridge segment articulates vertically with respect to said distal end displacement of said first and second end segments and the shape of said bridge segment articulates through a sequence of predetermined shapes whereby the external force exerted on said first and second end segments by said housing during retraction of said wire into said housing collapses said bridge segment through a sequence of vertically articulating predetermined shapes and upon extension of said wire from said housing said bridge segment of said electrode loop expands through a sequence of vertically articulating predetermined shapes;
   (d) means for electrically connecting said shaft member to a power supply.

2. The electrosurgical instrument recited in claim 1 wherein said housing has a fluid port communicating with said cavity defining a single flow path for the irrigation or evacuation of fluid and valve means for selectively controlling the flow of fluid through said single flow path.

3. An electrosurgical selectively controllable loop electrode for laparoscopic surgery comprising:
   (a) a housing having a longitudinal axis, a proximate and distal end, and an axially extending cavity forming a passageway therethrough;
   (b) a shaft member having a proximate and distal end carried by said housing and Slideably mounted within said cavity to permit axial and rotational displacement of said shaft member relative to said housing;
   (c) a wire electrode having a first end segment and a second end segment where said first and second end segments are in electrical communication with said shaft member and extend distally of said shaft member, said wire electrode having a bridge segment integrally interconnecting said first and second end segments forming a loop;
   (d) bias means carried by said shaft member and in sufficient bearing engagement with said first and second end segments for resiliently biasing said end segments such that external forces exerted by said housing on said bias means during proximate retraction of said electrode wire into said cavity of said housing collapses said loop through a sequence of predetermined shapes of decreasing concavity and upon extension of said wire electrode from said cavity distally of said housing expands said loop through a sequence of predetermined shapes of increasing concavity, said bias means comprises a pair of leaf springs of predetermined curvature having a distal and proximate end where the proximate end of each said spring is rigidly attached to said shaft member adjacent the distal end thereof and where said springs are internally biased to open upon extension of said springs distally from said housing cavity and to close upon external force exerted by said housing against said springs during retraction into said housing cavity.

4. The electrosurgical instrument recited in claim 3 wherein the leaf springs have an infinite radius of curvature.

5. The electrosurgical instrument recited in claim 3 wherein the curvature of said leaf springs is convex relative to said longitudinal axis.

6. The electrosurgical instrument recited in claim 3 where the curvature of said leaf springs is concave relative to said longitudinal axis.

7. The electrosurgical instrument recited in claim 4 wherein said housing has a fluid port communicating with said cavity defining a single flow path for the irrigation or evacuation of fluid and valve means for selectively controlling the flow of fluid through said single flow path.

8. The electrosurgical instrument recited in claim 5 wherein said housing has a fluid port communicating with said cavity defining a single flow path for the irrigation or evacuation of fluid and valve means for selectively controlling the flow of fluid through said single flow path.

9. The electrosurgical instrument recited in claim 6 wherein said housing has a fluid port communicating with said cavity defining a single flow path for the irrigation or evacuation of fluid and valve means for selectively controlling the flow of fluid through said single flow path.

* * * * *